(12) United States Patent
Osypka

(10) Patent No.: US 6,892,087 B2
(45) Date of Patent: May 10, 2005

(54) VASCULAR INTRODUCER WITH MAPPING CAPABILITIES

(75) Inventor: Thomas P. Osypka, Palm Harbor, FL (US)

(73) Assignee: Oscor Inc., Palm Harbor, FL (US)

(*) Notice: Subject to any disclaimer, the term of this patent is extended or adjusted under 35 U.S.C. 154(b) by 618 days.

(21) Appl. No.: 10/000,647

(22) Filed: Nov. 1, 2001

(65) Prior Publication Data

US 2003/0083560 A1 May 1, 2003

(51) Int. Cl.7 .................................. A61B 5/04
(52) U.S. Cl. ................................ 600/374
(58) Field of Search ..................... 600/373, 374, 600/381, 466, 471, 481; 604/93.01, 96.01, 97.03

(56) References Cited

U.S. PATENT DOCUMENTS

| | | | |
|---|---|---|---|
| 5,038,789 A | * | 8/1991 | Frazin ........................ 600/471 |
| 5,409,009 A | | 4/1995 | Olson |
| 5,738,683 A | | 4/1998 | Osypka |
| 5,836,875 A | * | 11/1998 | Webster, Jr. ................ 600/374 |
| 5,860,920 A | | 1/1999 | McGee et al. |
| 6,216,043 B1 | | 4/2001 | Swanson et al. |
| 6,233,491 B1 | | 5/2001 | Kordis et al. |
| 6,251,093 B1 | * | 6/2001 | Valley et al. ............ 604/97.03 |
| 6,254,599 B1 | | 7/2001 | Lesh et al. |
| 6,277,108 B1 | | 8/2001 | McBroom et al. |

* cited by examiner

Primary Examiner—George Manuel
(74) Attorney, Agent, or Firm—Scott D. Wofsy; Edwards & Angell, LLP

(57) ABSTRACT

A percutaneous vascular introducer is disclosed which includes a dilator having an elongated tubular body defining opposed proximal and distal end portions, the distal end portion of the dilator having, among other things, radiopaque characteristics to facilitate the safe placement of the distal tip of the dilator, and an elongated sheath having an interior lumen dimensioned and configured to accommodate the dilator.

33 Claims, 7 Drawing Sheets

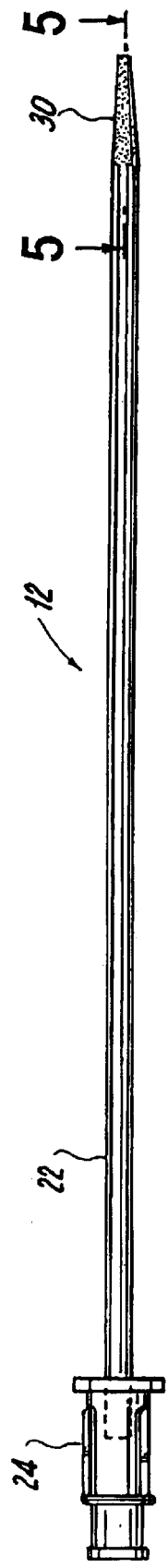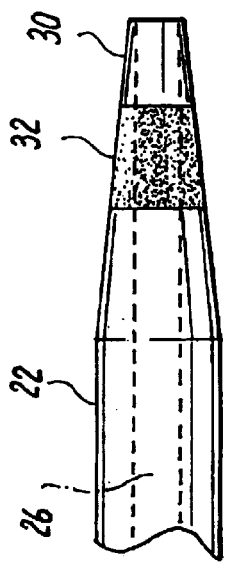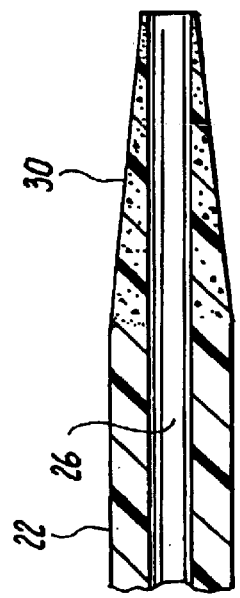
Fig. 2
Fig. 4
Fig. 3
Fig. 5

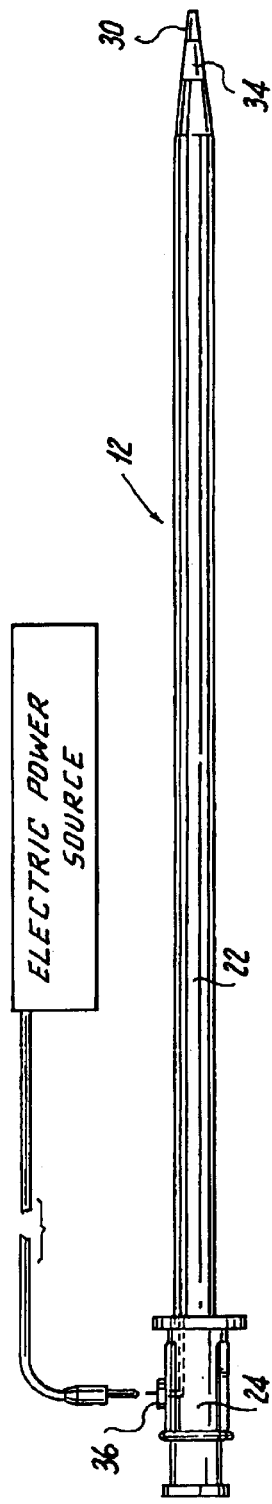
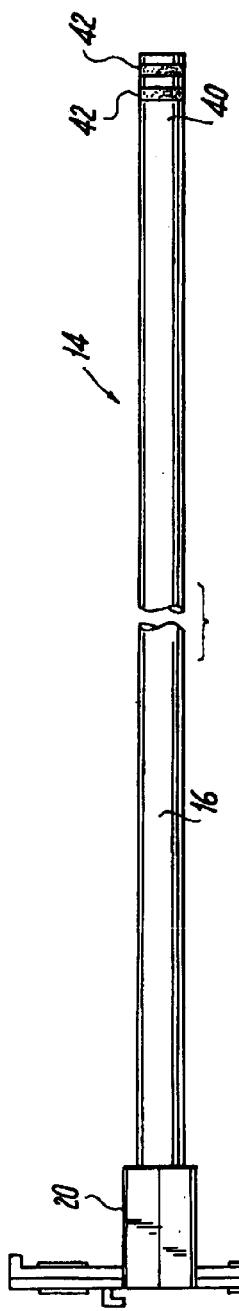
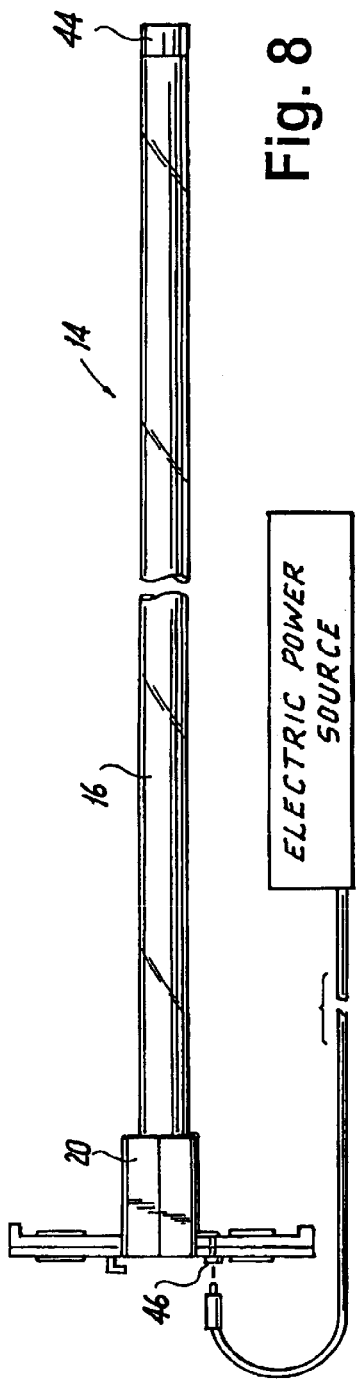
Fig. 6
Fig. 7
Fig. 8

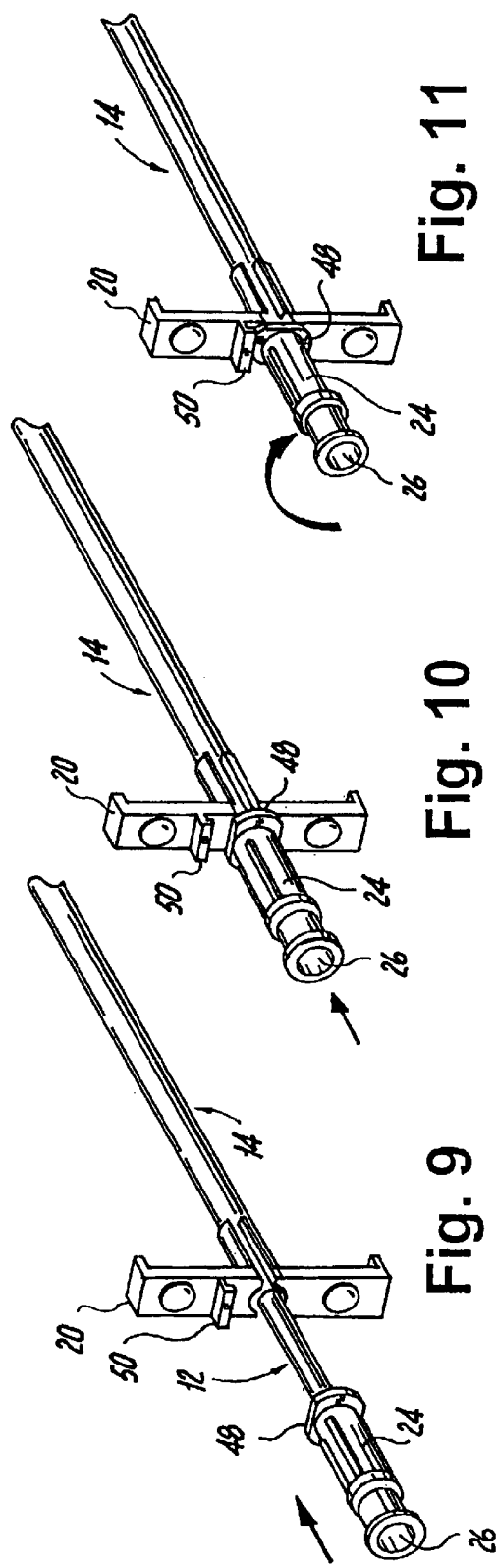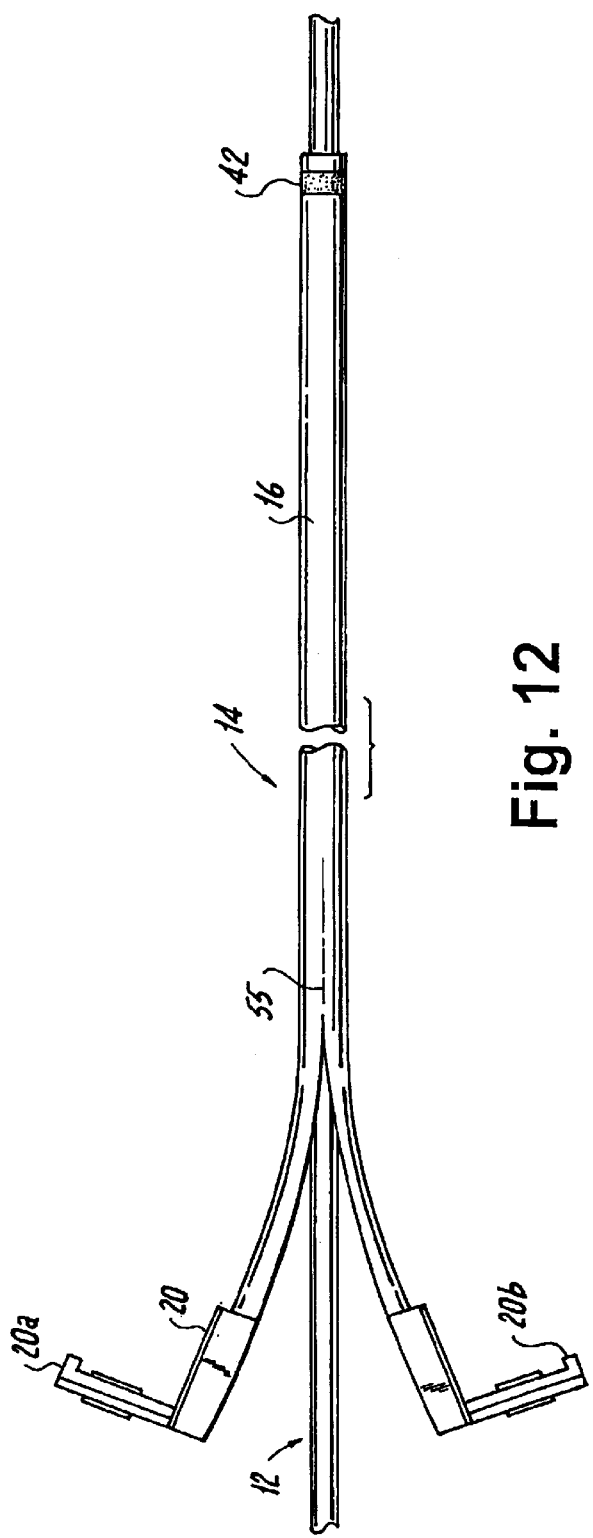

VASCULAR INTRODUCER WITH MAPPING CAPABILITIES

BACKGROUND OF THE INVENTION

1. Field of the Invention

The subject invention is directed to a device for introducing surgical devices into blood vessels, and more particularly, to a vascular introducer with mapping capabilities to facilitate the safe placement of the introducer within a blood vessel.

2. Background of the Related Art

Devices for assisting the percutaneous introduction and implantation of diagnostic or therapeutic instrumentation into the body during a surgical procedure are well known in the art. Percutaneous introducers generally include a dilator having a tapered distal tip for penetrating an incision and a tubular sheath having a lumen for accommodating the dilator. The sheath and dilator are locked together so as not to become separated during introduction. Once the introducer has been advanced to the surgical site, the dilator is unlocked and withdrawn. The sheath then becomes a pathway for the introduction of a diagnostic or therapeutic device into the patient's body. An example of a prior art percutaneous introducer is disclosed in U.S. Pat. No. 4,512,351 to Pohndorf.

Introducers for placing implantable devices such as cardiovascular catheters, cardiac pacing leads or defibrillation leads into the vasculature of a patient are well known. Typically, the sheath of a vascular introducer is about between 14 cm and 25 cm in length, and the dilator has a length of about between 16 cm and 27 cm. Vascular introducers used for placing leads or catheters directly into the coronary sinus of the heart are typically longer and, having lengths in excess of 35 cm. These longer vascular introducers must be placed with great caution, since the pointed tip of the dilator can damage or even puncture the interior wall of the heart.

U.S. Pat. No. 6,277,108 to McBroom et al. discloses a vascular introducer system that includes an elongated sheath with a marker band that allows the sheath to be viewed under fluoroscopy while inserted within a patient so as to permit a practitioner to identify the location of the introducer relative to the location of the intended implant device. This prior art introducer does not however, provide any means for identifying the distal end of the dilator, which is the part of the introducer that can cause the most trauma to the heart if misplaced or misdirected during insertion.

It would be beneficial therefore, to provide a percutaneous vascular introducer configured to facilitate the safe placement of an implantable diagnostic or therapeutic device into the body during a surgical procedure that is adapted and configured to permit a practitioner to identify the distal end of the dilator within the patients heart.

SUMMARY OF THE INVENTION

The subject invention is directed to a percutaneous vascular introducer for safely placing therapeutic surgical devices at a desired location, such as, for example, in the coronary sinus of the heart. The introducer includes a dilator having an elongated tubular body defining opposed proximal and distal end portions and an elongated sheath having an interior lumen dimensioned and configured to accommodate the dilator and provide a pathway for the introduction of an endocardial device in the absence of the dilator. The dilator has an axial lumen extending therethrough to accommodate a guidewire used to direct the introducer to a desired location. Preferably, the proximal portion of the dilator and the proximal portion the sheath include locking means to fasten the dilator to the sheath, and the sheath includes means to facilitate separation thereof from the dilator and a handle to facilitate manipulation thereof.

The distal end portion of the dilator includes a tapered distal tip having radiopaque characteristics to facilitate safe positioning of the distal tip of the dilator within a patient's body while under x-ray vision or when viewed by fluoroscopic means. In one embodiment of the invention, the tapered distal portion of the dilator is formed from a plastic material having a radiopaque material combined therewith, and in another embodiment of the invention, the tapered distal portion of the dilator has at least one radiopaque band of material extending thereabout. It is also envisioned that the tapered distal portion of the dilator is formed from a thermoplastic plastic material that is softer than the thermoplastic material making up the remainder of the dilator, so that the distal portion of the dilator is sufficiently flexible to avoid causing undue trauma to the interior wall of the heart.

In another embodiment of the subject invention, the tapered distal portion of the dilator is electrically conductive to facilitate cardiac mapping. It is envisioned that the electrical conductivity feature may be provided either alone or in combination with the radiopacity feature. Alternatively, the tapered distal portion of the dilator includes means for measuring arterial blood flow parameters to facilitate placement of the dilator, such as a pulse Doppler sensor or transit-time sensor. It is envisioned that this feature may be provided either alone or in combination with either one or both of the radiopacity feature, and the electrical conductivity feature.

In another embodiment of the invention, a distal portion of the sheath has radiopaque characteristics to facilitate placement thereof. In such an embodiment, the distal portion of the sheath may have at least one radiopaque band of material extending thereabout. It is also envisioned that in an embodiment of the invention, the distal portion of the sheath is electrically conductive to facilitate cardiac mapping.

The subject invention is further directed to a bipolar percutaneous vascular introducer having cardiac mapping capabilities. The introducer includes a dilator having an elongated tubular body defining opposed proximal and distal end portions. The distal end portion of the dilator includes an electrically conductive tapered distal tip defining a first pole to facilitate cardiac mapping. The introducer further includes an elongated sheath having an interior lumen dimensioned and configured to accommodate the dilator and including an electrically active distal portion defining a second pole to facilitate cardiac mapping. In such an embodiment, the tapered distal portion of the dilator as well as the distal portion of the sheath can have radiopaque characteristics to facilitate the safe placement thereof while viewed by x-ray or when viewed by fluoroscopic means. It is also envisioned that, the tapered distal portion of the dilator can include means for measuring arterial blood flow parameters to facilitate placement of the dilator.

These and other aspects of the vascular introducer of the subject invention and the method of using the same will become more readily apparent to those having ordinary skill in the art from the following detailed description of the invention taken in conjunction with the drawings described hereinbelow.

BRIEF DESCRIPTION OF THE DRAWINGS

So that those having ordinary skill in the art to which the subject invention pertains will more readily understand how to make and use the apparatus of the subject invention, preferred embodiments thereof will be described in detail hereinbelow with reference to the drawings, wherein:

FIG. 2 is a side elevational view in cross-section of the dilator of the subject invention, wherein the distal portion of the dilator has a radiopaque band associated therewith;

FIG. 3 is a enlarged localized view of the distal tip portion of the dilator of FIG. 2;

FIG. 4 is a side elevational view of the dilator of the subject invention, wherein the distal portion of the dilator is formed from a material that is impregnated with a radiopaque material;

FIG. 5 is a enlarged localized view of the distal tip portion of the dilator of FIG. 4, in cross-section;

FIG. 6 is a side elevational view of the dilator of the subject invention, wherein the distal portion of the dilator includes an electrode operatively associated with an electrical power source or a metering unit;

FIG. 7 is a side elevational view of the sheath of the subject invention, wherein the distal portion of the sheath has a radiopaque band associated therewith;

FIG. 8 is a side elevational view of the sheath of the subject invention, wherein the distal portion of the sheath includes an electrode operatively associated with an electrical power source or a metering unit;

FIGS. 9–11 illustrate the operative steps for interlocking the proximal portions of the dilator and the sheath to one another by way of an exemplary fastening system;

FIG. 12 illustrates the manner in which the sheath is pealed away from the dilator by separating the handles along a parting line;

DETAILED DESCRIPTION OF PREFERRED EMBODIMENTS

In the specification that follows the term "distal" shall refer to the end of the vascular introducer nearest to the surgical site, while the term "proximal" shall refer to the end of the vascular introducer farthest from the surgical site.

Figure 1:
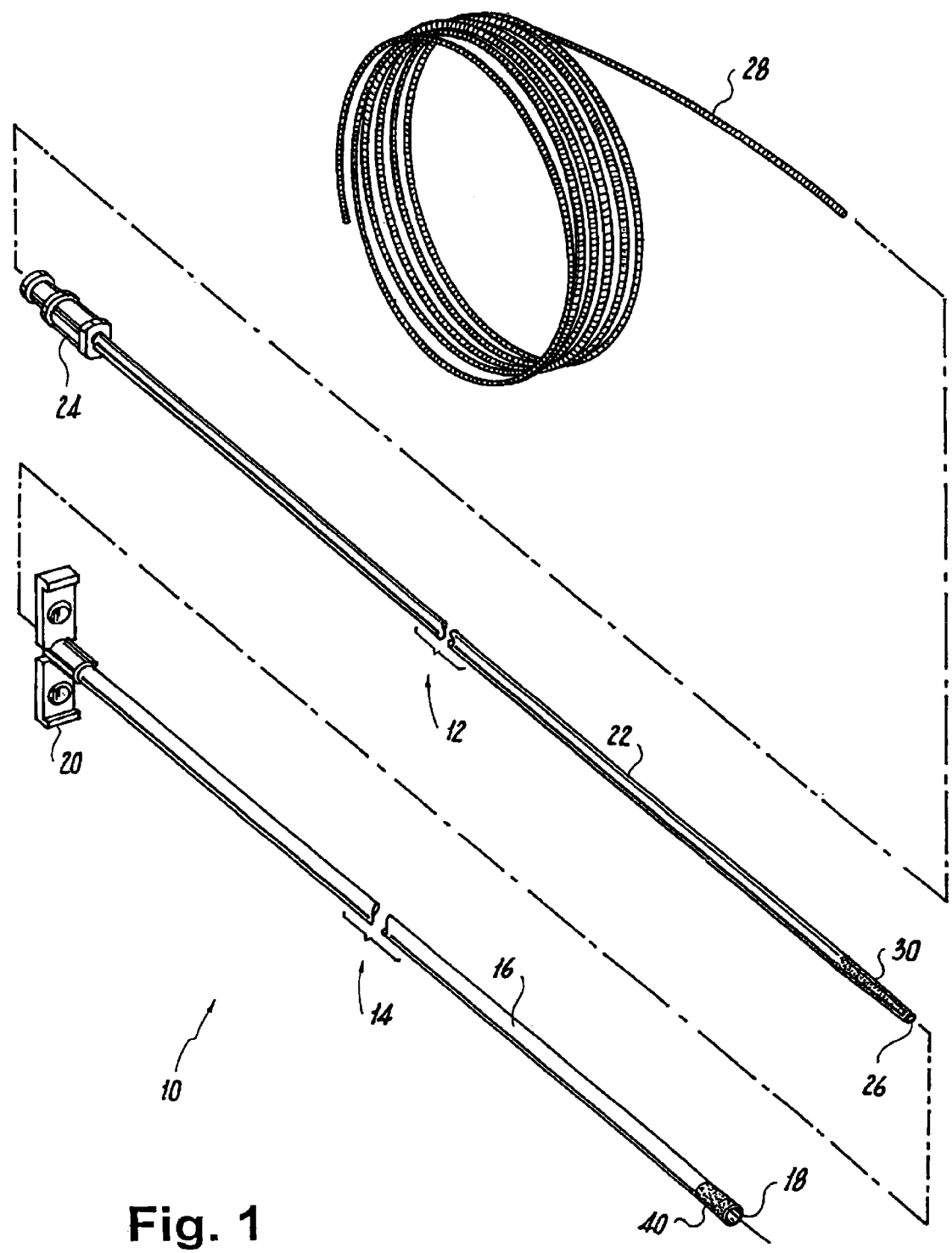
FIG. 1 is a perspective view of a vascular introducer set constructed in accordance with a preferred embodiment of the subject invention which includes an elongated dilator having a central lumen for receiving a guidewire and an elongated sheath having an interior lumen for accommodating the dilator, wherein the distal portions of the dilator and the sheath have radiopaque characteristics.

Referring now to the drawings wherein like reference numerals identify similar structural elements of the device disclosed herein, there is illustrated in FIG. 1 a vascular introducer constructed in accordance with a preferred embodiment of the subject invention and designated generally by reference numeral 10. Vascular introducer 10 is adapted and configured for percutaneous introduction into the vasculature of a patient to facilitate the safe placement of a therapeutic or diagnostic surgical devices at a desired location. For example, the introducer 10 is particularly adapted for the introduction and placement of a cardiac lead or catheter. More particularly, the vascular introducer of the subject invention is dimensioned and configured for introducing and placing cardiac leads or catheters into the coronary sinus of the heart, as shown for example in FIG. 20.

Referring to FIG. 1, vascular introducer 10 has two primary components formed from a bio-compatible plastic material such as low density polyethylene or high density polyethylene (LDPE or HDPE), including a dilator 12 and an elongated sheath 14. The elongated sheath 14 is defined by a thin-walled tubular body 16 having opposed proximal and distal end portions and an interior lumen 18. Lumen 18 is dimensioned and configured to accommodate the dilator 12 during percutaneous introduction into a blood vessel, and to accommodate the passage of cardiac catheters and leads therethrough for placement in the absence of the dilator. A generally T-shaped handle 20 is operatively associated with the proximal end of tubular body 16 and the distal end of the body portion has a slightly tapered about the axial centerline of the sheath.

The dilator 12 is defined by an elongated tubular body 22 having opposed proximal and distal end portions. A reception sleeve 24 is provided at the proximal end of tubular body 22 which defines an entry port into an axial lumen 26 of tubular body 22. The axial lumen 26 is adapted to accommodate an elongated flexible guidewire 28 which may be used to ease placement of the vascular introducer 10 during a surgical procedure. The distal portion of tubular body 22 defines a tapered tip 30 which serves to ease the percutaneous entry through an incision.

Figure 20:
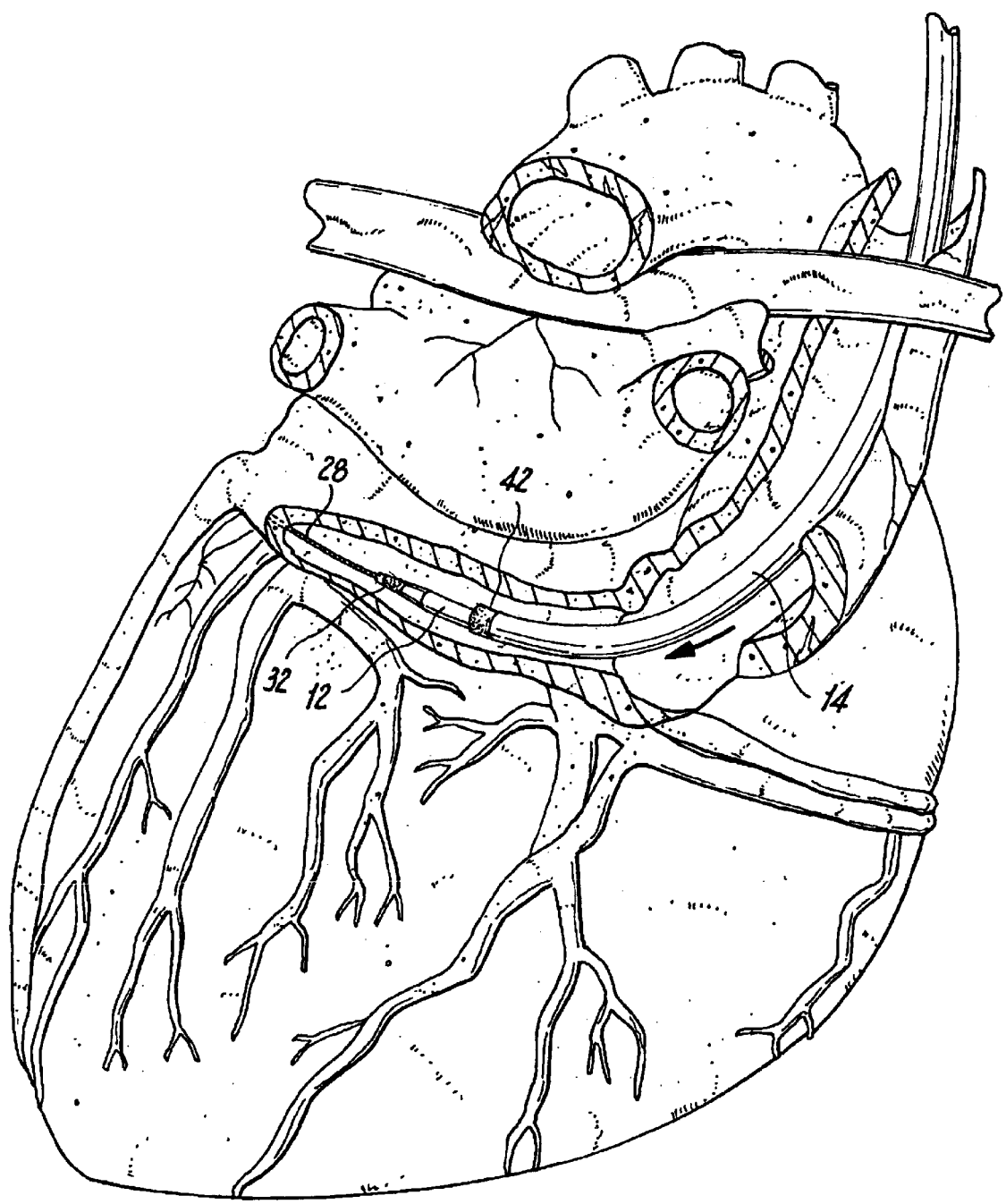
FIG. 20 illustrates the safe positioning of the introducer of the subject invention into the cardiac sinus with the radiopaque distal portions of the introducer set illuminated by x-ray or by fluoroscopic means.

Preferably, the dilator 12 of vascular introducer 10 has an operative length of at least about 35 cm and the sheath 14 of vascular introducer 10 has an operative length of about 32 cm. Thus, vascular introducer 10 of the subject invention is appropriately sized for advancement into the coronary sinus for placement of a lead, as shown in FIG. 20.

In accordance with a preferred embodiment of the subject invention, the tapered distal tip 30 of dilator 12 has radiopaque characteristics to facilitate the safe positioning of the distal tip of the dilator within a patient's body while under x-ray vision or when viewed by fluoroscopic means. In one embodiment, the tapered distal tip 30 of dilator 12 is formed from a material having a radiopaque material combined therewith, as shown in FIGS. 4 and 5. For example, the bio-compatible plastic material from which the body of the dilator is formed can include barium sulfate or a similar radiopaque material. In another embodiment, illustrated in FIGS. 2 and 3, the tapered distal tip 30 of the dilator 12 includes at least one radiopaque band 32 extending thereabout. In such an instance, the band of material would consist of a metallic material such as stainless steel or platinum. As illustrated the band 32 is positioned in such a manner so as to create a smooth continuous tapered surface at the distal end of the dilator. It is envisioned that a plurality of axially spaced apart radiopaque bands could be provided along the tapered tip to aide in visualization and placement of the introducer.

In embodiments of the subject invention, the tapered distal 30 of dilator 12 is electrically conductive to facilitate cardiac mapping. More particularly, as shown in FIG. 6, the distal tip 30 of dilator 12 includes an electrode 34 used as a sensor or scanner, much like a conventional pacing/sensing lead, to map the exact location of the dilator tip within the myocardium. Preferably, the sensor electrode 34 is adapted to locate the coronary sinus, and more particular, the opening to the coronary vein, to ensure proper placement of a coronary sinus lead. This is accomplished by measuring electrical potentials at various locations within the heart. The sensing electrode 34 may be formed from a conductive material such as platinum, iridium or alloys thereof. In this instance, the proximal portion of the dilator 12, and in particular, the sleeve 24 includes an electrical connector 36. The electrical connector 36 is operatively connected to the electrode/sensor 34 by conventional means such as, for example, a multifilar conductor coil or the like. The connector 36 is adapted and configured to communicate with an external electrocardiogram device providing a source of power for the electrode/sensor. The connector 36 can take the form of any type of known connector commonly utilized in the art.

Referring to FIG. 1, in an embodiment of the subject invention, a distal portion 40 of the sheath 14 has radiopaque characteristics to facilitate safe placement of the introducer within the myocardium. As in the case of the radiopaque dilator 12 described above, the plastic material from which the distal portion 40 of the sheath 14 is formed can include barium sulfate or a similar radiopaque material. Alternatively, in an embodiment of the subject invention, one or more radiopaque bands 42 may be operatively associated with the distal portion 40 of sheath 14, as shown for example in FIG. 7 to enhance visualization and placement of the sheath within the myocardium.

Referring to FIG. 8, in accordance with an embodiment of the subject invention, the distal portion 40 of sheath 14 is electrically active and includes a sensing electrode 44 to facilitate cardiac mapping. The sensing electrode 44 may be formed from a material such as platinum, iridium or alloys thereof. In this instance, the proximal portion of the sheath 14, and in particular the handle 20, includes an electrical connector 46. The electrical connector 46 is operatively connected to the sensing electrode 44 by conventional means such as, for example, a multifilar conductor coil or the like, and is adapted to communicate with an external source of power and metering.

In instances wherein the vascular introducer 10 of the subject invention includes a dilator 12 having a distal sensing electrode 34 as in FIG. 6, and sheath 14 having a distal sensing electrode 44, the introducer 10 functions as a bipolar sensing device. More particularly, in such an instance, the electrically active distal tip 30 of the dilator 12 shown in FIG. 6 defines a first pole, and the electrically active distal portion 40 of the sheath 14 shown in FIG. 8 defines a second pole to facilitate cardiac mapping. It is also envisioned that either the electrically active distal portion 30 of the dilator 12 or the electrically active distal portion 40 of the sheath 14 may have a bipolar or multi-polar configuration to facilitate cardiac mapping or scanning of regions of the heart be measuring electrical potentials.

Referring to FIGS. 9–11, the proximal portion of the dilator 12 and the proximal portion the sheath 14 preferably include cooperative interlocking structures to fasten the dilator to the sheath. As illustrated, the interlocking structures associated with lead 10 include a radial flange 48 associated with the reception sleeve 24 at the proximal end of dilator 12 and a keeper tab 50 associated with the handle 20 at the proximal end of sheath 14. In use, upon insertion of the dilator 12 into the lumen of the sheath 14, and rotation of the dilator 12 relative to the sheath 14, the radial flange 48 is received and retained by the keeper tab 50. Other interlocking structures may be employed to secure the sheath and dilator together such as structures dimensioned for an interference fit or structures that include cooperative threads. It should be understood that the locking mechanism illustrated herein in should in no way be construed to limit the subject disclosure in any way, as it is simply illustrative of an exemplary locking system for the introducer.

Referring to FIG. 12, in accordance with an embodiment of the subject invention, the thin-walled tubular sheath 14 is configured as a peelable or splitable sheath to facilitate the separation of the sheath from the dilator 12. More particularly, the handle 20 includes opposed handle portions 20a and 20b separated by a weakened mid-portion and the tubular body 16 of the sheath 14 includes diametrically score lines that extend along the length of the sheath 14 which facilitate separation of the tubular body 16 into two parts. Peelable sheaths are known in the art and are disclosed for example in U.S. Pat. No. 4,512,351 to Pohndorf and U.S. Pat. No. 6,277,108 to McBroom et al., the disclosures of which are incorporated herein by reference.

Figure 13:
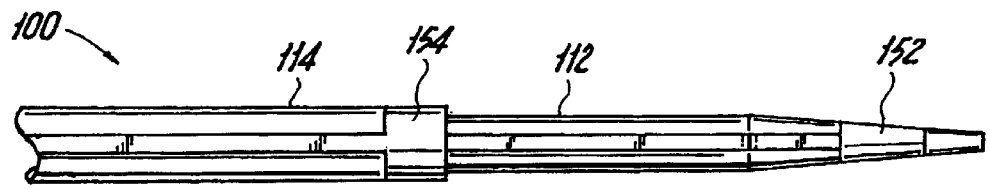
FIGS. 13–18 illustrate distal portions of various embodiments of the vascular introducer of the subject invention wherein each embodiment has different features for facilitating mapping within the myocardium.
Figure 14:
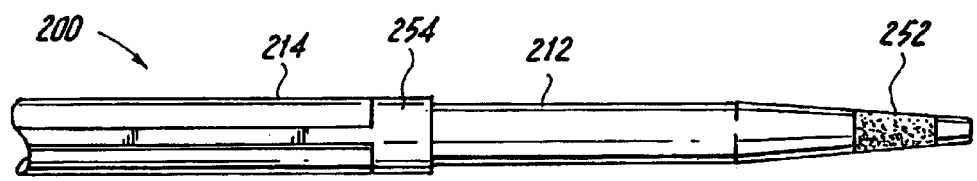
Figure 15:
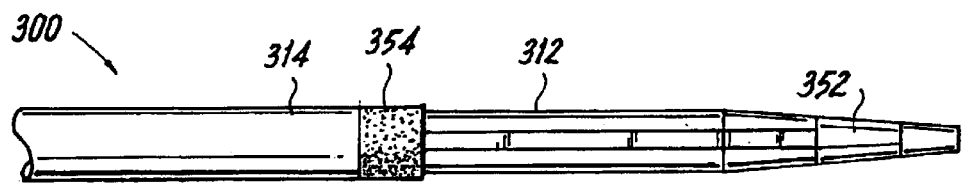
Figure 16:

Referring now to FIGS. 13–18, there are illustrated several variants of the vascular introducer of the subject invention. FIG. 13 depicts a vascular introducer 100 that includes a dilator 112 having a distal sensing electrode 152 and a sheath 114 having a distal sensing electrode 154. FIG. 14 depicts a vascular introducer 200 that includes a dilator 212 having a distal radiopaque band 252 and a sheath 214 having a distal sensing electrode 254. FIG. 15 depicts a vascular introducer 300 that includes a dilator 312 having a distal sensing electrode 352 and a sheath 314 having a distal radiopaque band 354. FIG. 16 depicts a vascular introducer 400 that includes a dilator 412 having a distal sensing electrode 452a and a distal radiopaque tip portion 452b adjacent thereto, and a sheath 414 having a distal sensing electrode 454.

Figure 17:
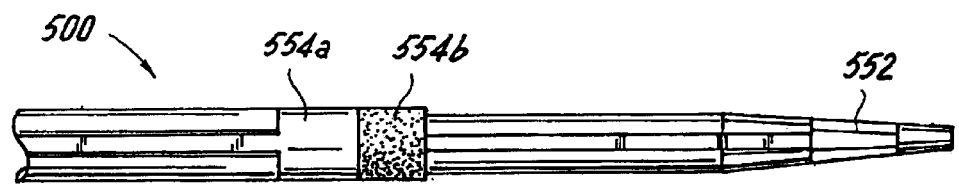
Figure 18:
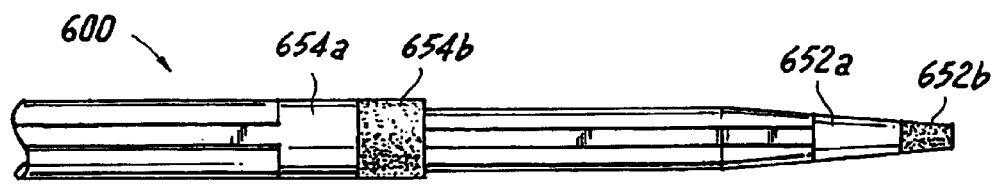

FIG. 17 depicts a vascular introducer 500 that includes a dilator 512 having a distal sensing electrode 552 and a sheath 514 having a distal sensing electrode 554a and a distal radiopaque tip portion 554b adjacent thereto. FIG. 18 depicts a vascular introducer 600 that includes a dilator 612 having a distal sensing electrode 652a and a distal radiopaque tip portion 652b adjacent thereto, and a sheath 614 having a distal sensing electrode 654a and a distal radiopaque tip portion 654b adjacent thereto. Other variants are also possible and are within the scope of the subject disclosure.

Figure 19:
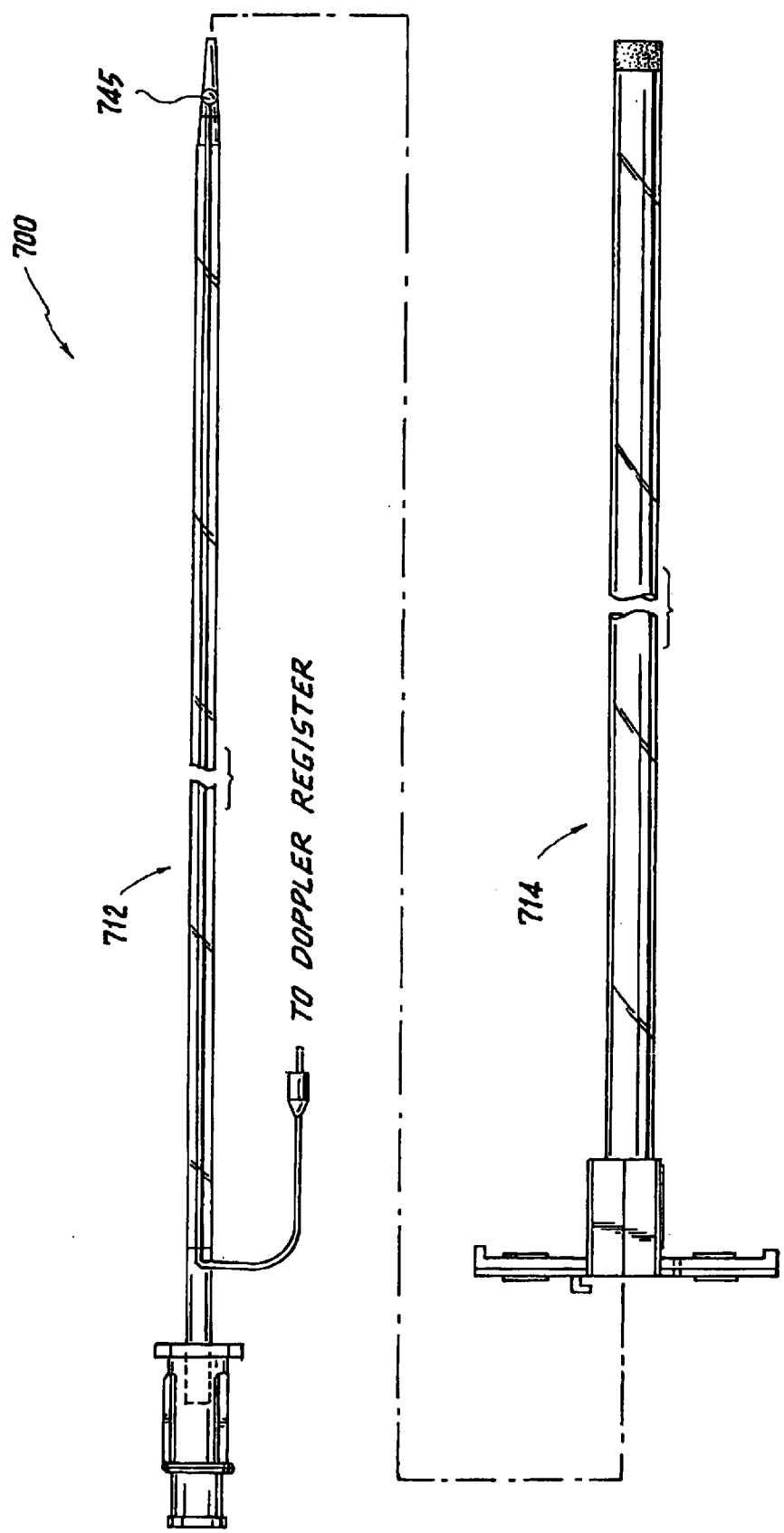
FIG. 19 is side elevational view of the dilator and sheath of the subject invention, wherein the distal portion of the dilator includes a Doppler sensor and the distal portion of the sheath is impregnated with a radiopaque material.

Referring now to FIG. 19, there is illustrated another embodiment f the vascular introducer of the subject invention designated generally by reference numeral 700 including a dilator 712 and a tubular sheath 714 having radiopaque characteristics. The distal portion of the dilator 712 includes a sensor 745 for monitoring blood flow. The flow sensor 745 can take the form of an ultrasonic pulse Doppler sensor, transit-time sensor or a similar sensor. Such sensors are knows in the art as disclosed for example in U.S. Pat. No. 5,409,009 to Olson, the disclosure of which is herein incorporated by reference in its entirety.

In embodiments of the vascular introducer described and illustrated herein, it is envisioned that the tapered distal portion of the dilator, perhaps a portion about approximately 2 cm in length, may be formed from a thermoplastic plastic material (e.g., LDPE or HDPE) that is softer than the thermoplastic material (e.g., LDPE or HDPE) making up the remainder of the dilator. More particularly, the durometer of the softer distal portion would be less than the durometer of the remaining proximal portion of the dilator. In so doing, the tapered distal portion of the dilator would be sufficiently flexible so as not to cause undue trauma to the interior wall of the heart during insertion, but it would have sufficient rigidity to facilitate percutaneous insertion of the introducer. Such a structure could be formed using thermoplastic extrusion techniques that are presently known in the art.

Although the vascular introducer of the subject invention has been described with respect to a preferred embodiment, those skilled in the art will readily appreciate that changes and modifications may be made thereto without departing from the spirit and scope of the present invention.

What is claimed is:

1. A percutaneous vascular introducer having mapping capabilities comprising:
   a) a dilator having an elongated tubular body defining opposed proximal and distal end portions, the distal end portion of the dilator including a tapered distal tip having radiopaque characteristics to facilitate safe positioning of the distal tip of the dilator within a patient's body, and wherein the dilator includes electrically conductive means to facilitate cardiac mapping; and
   b) an elongated sheath having an interior lumen dimensioned and configured to accommodate the dilator and provide a pathway for the introduction of an endocardial device in the absence of the dilator.

2. A percutaneous vascular introducer as recited in claim 1, wherein the dilator has an axial lumen extending therethrough to accommodate a guidewire.

3. A percutaneous vascular introducer as recited in claim 1, wherein the tapered distal portion of the dilator is formed from a plastic material having a radiopaque material combined therewith.

4. A percutaneous vascular introducer as recited in claim 1, wherein the tapered distal portion of the dilator has at least one radiopaque band of material extending thereabout.

5. A percutaneous vascular introducer as recited in claim 1, wherein a distal portion of the sheath has radiopaque characteristics to facilitate placement thereof.

6. A percutaneous vascular introducer as recited in claim 5, wherein the distal portion of the sheath has at least one radiopaque band of material extending thereabout.

7. A percutaneous vascular introducer as recited in claim 1, wherein a distal portion of the sheath is electrically conductive to facilitate cardiac mapping.

8. A percutaneous vascular introducer as recited in claim 7, wherein the proximal portion of the sheath includes an electrical connector operatively associated with the electrically conductive distal portion of the sheath.

9. A percutaneous vascular introducer as recited in claim 1, wherein the proximal portion of the dilator and the proximal portion the sheath include locking means to fasten the dilator to the sheath.

10. A percutaneous vascular introducer as recited in claim 1, wherein the sheath includes means to facilitate separation thereof from the dilator.

11. A percutaneous vascular introducer as recited in claim 1, wherein the proximal portion of the dilator includes an electrical connector operatively associated with the electrically conductive distal tip of the dilator.

12. A percutaneous vascular introducer as recited in claim 1, wherein the proximal portion of the sheath includes a handle to facilitate manipulation thereof.

13. A percutaneous vascular introducer as recited in claim 1, wherein the tapered distal portion of the dilator includes means for measuring arterial blood flow parameters to facilitate placement of the dilator.

14. A percutaneous vascular introducer as recited in claim 1, wherein the tapered distal portion of the dilator is formed form a material that is softer than the material from which the remainder of the dilator is formed.

15. A percutaneous vascular introducer having mapping capabilities comprising:
   a) a dilator having an elongated tubular body defining opposed proximal and distal end portions, the distal end portion of the dilator including an electrically conductive tapered distal tip defining means to facilitate cardiac mapping; and
   b) an elongated sheath having an interior lumen dimensioned and configured to accommodate the dilator and provide a pathway for the introduction of an endocardial device in the absence of the dilator.

16. A percutaneous vascular introducer as recited in claim 15, wherein the dilator has an axial lumen extending therethrough to accommodate a guidewire.

17. A percutaneous vascular introducer as recited in claim 15, wherein the tapered distal portion of the dilator has radiopaque characteristics.

18. A percutaneous vascular introducer as recited in claim 17, wherein the tapered distal tip portion of the dilator is formed from a plastic material having a radiopaque material combined therewith.

19. A percutaneous vascular introducer as recited in claim 17, wherein the tapered distal portion of the dilator has at least one radiopaque band of material extending thereabout.

20. A percutaneous vascular introducer as recited in claim 15, wherein a distal portion of the sheath has radiopaque characteristics to facilitate placement thereof.

21. A percutaneous vascular introducer as recited in claim 20, wherein the distal portion of the sheath has at least one radiopaque band of material extending thereabout.

22. A percutaneous vascular introducer as recited in claim 15, wherein a distal portion of the sheath is electrically conductive to facilitate cardiac mapping.

23. A percutaneous vascular introducer as recited in claim 15, wherein the proximal portion of the dilator and the proximal portion the sheath include locking means to fasten the dilator to the sheath.

24. A percutaneous vascular introducer as recited in claim 15, wherein the sheath includes means to facilitate separation thereof from the dilator.

25. A percutaneous vascular introducer as recited in claim 15, wherein the proximal portion of the dilator includes an electrical connector operatively associated with the electrically conductive distal tip of the dilator.

26. A percutaneous vascular introducer as recited in claim 25, wherein the proximal portion of the sheath includes an electrical connector operatively associated with the electrically conductive distal portion of the sheath.

27. A percutaneous vascular introducer as recited in claim 15, wherein the proximal portion of the sheath includes a handle to facilitate manipulation thereof.

28. A percutaneous vascular introducer as recited in claim 15, wherein the tapered distal portion of the dilator includes means for measuring arterial blood flow parameters to facilitate placement of the dilator.

29. A percutaneous vascular introducer as recited in claim 15, wherein the tapered distal portion of the dilator is formed form a material that is less stiff than the material from which the remainder of the dilator is formed.

30. A bipolar percutaneous vascular introducer having cardiac mapping capabilities comprising:
   a) a dilator having an elongated tubular body defining opposed proximal and distal end portions, the distal end portion of the dilator including an electrically conductive tapered distal tip having means defining a first pole to facilitate cardiac mapping; and b) an elongated sheath having an interior lumen dimensioned and configured to accommodate the dilator and provide a pathway for the introduction of an endocardial device in the absence of the dilator, the sheath including an electrically active distal portion having means defining a second pole to facilitate cardiac mapping.

31. A bipolar percutaneous vascular introducer as recited in claim 30, wherein the tapered distal portion of the dilator has radiopaque characteristics to facilitate placement thereof.

32. A bipolar percutaneous vascular introducer as recited in claim 30, wherein the distal portion of the sheath has radiopaque characteristics to facilitate placement thereof.

33. A bipolar percutaneous vascular introducer as recited in claim 30, wherein the tapered distal portion of the dilator includes means for measuring arterial blood flow parameters to facilitate placement of the dilator.

* * * * *